(12) United States Patent
Shuster et al.

(10) Patent No.: US 10,729,877 B2
(45) Date of Patent: *Aug. 4, 2020

(54) TREATMENT OF PHANTOM LIMB SYNDROME AND OTHER SEQUELAE OF PHYSICAL INJURY

(71) Applicant: IDEAFLOOD, INC., Carson City, NV (US)

(72) Inventors: Gary Stephen Shuster, Vancouver (CA); Brian Mark Shuster, Vancouver (CA); Charles Marion Curry, Jr., Fresno, CA (US); Dana Beth Shuster, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/870,446

(22) Filed: Jan. 12, 2018

(65) Prior Publication Data

US 2018/0133432 A1 May 17, 2018

Related U.S. Application Data

(63) Continuation of application No. 14/658,084, filed on Mar. 13, 2015, now Pat. No. 9,867,961.

(Continued)

(51) Int. Cl.
*A61M 21/02* (2006.01)
*A61F 2/54* (2006.01)
(Continued)

(52) U.S. Cl.
CPC .............. *A61M 21/02* (2013.01); *A61F 2/54* (2013.01); *A61F 2/72* (2013.01);
(Continued)

(58) Field of Classification Search
CPC .............. A61M 21/00–02; A61F 2/54; A61F 2002/5058–5064
See application file for complete search history.

(56) References Cited

U.S. PATENT DOCUMENTS

2011/0065505 A1 3/2011 Solanki et al.
2012/0004579 A1 1/2012 Lou et al.
(Continued)

FOREIGN PATENT DOCUMENTS

KR 101196960 B1 11/2012

OTHER PUBLICATIONS

Skillings; "Samsung shows off Youm flexible display," CNET, Jan. 9, 2013, retrieved on Jun. 5, 2017, https://www.cnet.com/news/samsung-shows-off-youm-flexible-display/.

*Primary Examiner* — Thaddeus B Cox
(74) *Attorney, Agent, or Firm* — Sherrie Flynn; Coleman & Horowitt LLP (57) ABSTRACT

Methods, systems and devices that provide a therapeutic solution to alleviate the pain and discomfort of phantom limb syndrome are disclosed. The methods and systems of the present invention generally comprise capturing data from recording devices operably coupled to a processor and/or computing device, the recording devices configured to capture data associated with intact portions of a missing limb, one or more intact limbs and/or portions of the environment surrounding the missing limb, identifying the data captured, generating a three-dimensional virtual image of the missing limb and the surrounding environment from the data captured, and displaying the three-dimensional virtual image and the portions of the surrounding environment to the amputee such that the missing limb appears intact. The present invention advantageously provides a therapeutic and more immediate solution to alleviate the pain and discomfort from phantom limb syndrome.

18 Claims, 5 Drawing Sheets

Related U.S. Application Data

(60) Provisional application No. 61/952,723, filed on Mar. 13, 2014.

(51) Int. Cl.
  *A61F 2/72*    (2006.01)
  *A61N 1/04*    (2006.01)
  *A61M 21/00*   (2006.01)
  *A61N 1/36*    (2006.01)
  *A61F 2/70*    (2006.01)

(52) U.S. Cl.
  CPC .. *A61F 2002/707* (2013.01); *A61M 2021/005* (2013.01); *A61M 2021/0011* (2013.01); *A61M 2021/0022* (2013.01); *A61M 2021/0055* (2013.01); *A61M 2021/0066* (2013.01); *A61M 2205/3653* (2013.01); *A61M 2205/502* (2013.01); *A61N 1/0456* (2013.01); *A61N 1/36025* (2013.01)

(56) References Cited

U.S. PATENT DOCUMENTS

| | | |
|---|---|---|
| 2012/0206577 A1 | 8/2012 | Guckenberger et al. |
| 2014/0114119 A1 | 4/2014 | Wiest |
| 2015/0054850 A1* | 2/2015 | Tanaka .................. G06T 11/00 345/633 |

* cited by examiner

TREATMENT OF PHANTOM LIMB SYNDROME AND OTHER SEQUELAE OF PHYSICAL INJURY

CROSS-REFERENCE TO RELATED APPLICATIONS

This application is a continuation of U.S. patent application Ser. No. 14/658,084, now U.S. Pat. No. 9,867,961, which claims the benefit under 35 U.S.C. § 119 (e) of U.S. Provisional Patent Application No. 61/952,723 filed Mar. 13, 2014. The text and contents of the aforementioned applications are hereby incorporated into this application by reference as if fully set forth herein.

FIELD OF INVENTION

The subject disclosure generally relates to the field of prosthetic limbs. Specifically, embodiments of the present invention relate to methods and devices for treating phantom limb syndrome, and methods for screening prosthetic limbs for amputees.

DISCUSSION OF THE BACKGROUND

For the purposes of this specification, the present invention will generally be described in relation to treating phantom limb syndrome (the ability to feel pain and/or sensations in a limb that no longer exists). However, the invention is not so limited and may be applied in a variety of other applications including, but not limited to phantom sensations that may be perceived in people who have survived strokes but have lost function in certain body parts, people who have had spinal cord, nerve, or other types of injury, or people who were born without limbs.

Frequently, people who have lost a body part experience pain or other physical sensations as a result of Phantom limb syndrome. When suffering from this ailment, people who are missing a limb feel pain as if the limb were there and hurting, itching, or otherwise needing attention, yet because the body part is not present, the body part cannot receive attention or treatment.

This section is provided for background purposes only. Nothing in this section is to be construed as admission as to whether such technology would be considered art relevant to the patentability of the present invention. Inclusion of technology and information in the section below is not an admission that it exists or is in development other than development by the inventors of the present invention.

Current treatment for Phantom limb syndrome is often ineffective and, even if effective, in nearly all cases involves an unacceptably long period before the patient feels sufficient relief. Conventional treatments include therapies such as mirror therapy (MT) and box mirror therapy, which are used with some limited success. However, it is often the case that any improvement seen in amputees occurs no faster than over several months and in some cases far longer. Additionally there may be different causes of phantom pain, and it is unclear which causes are efficaciously mitigated by MT. Indeed, MT appears to be, at best, only partially effective.

One of the ways that MT works is by tricking the amputee's brain into believing that the missing limb is still there and that they still have control over it. This happens when the amputee's brain associates the movement of the working limb with the movement of the limb that no longer exists. For instance, if a below-the-elbow amputee were to pretend that they were clapping using a box mirror, the amputee would see two clapping hands; one being a real hand and the other being a reflection. MT is limited because it requires, in most instances, that the amputee engage in exercises where a mirror image of the intact limb can be perceived. This system is imperfect, far from portable, and unable to present the patient with sufficient or appropriate input as would be necessary for fully effective treatment. MT has been implemented within a computing environment (as described in http://www.bbc.com/news/health-26327457). In that case, a digital representation of an arm is displayed on a computer monitor without the use of a mirror.

In any case, what does not exist in the art is a system, device, or method that alters data prior to its perception by the human sensory system, where the alteration is done in a manner that changes the human reaction to the data or the human's response to his or her environment. Very different from existing therapeutic solutions such as MT, the instant invention allows the amputee to actually control a virtual limb with the brain as opposed to tricking the brain into thinking that it is controlling a limb.

Consequently, there is a strong need for methods, systems and devices that provide a therapeutic and more immediate solution to alleviate pain and discomfort from phantom limb syndrome.

SUMMARY OF THE INVENTION

An amputee uses the present invention incorporating augmented reality ("AR"), and is presented with an intact virtual limb that appears to them identical to their pre-amputation limb. The virtual limb may be controllable by the user. Over time, the limb control may be reduced, the limb may be faded out, portions of the limb may be "amputated", or other modifications made so that the user's brain can adapt to the required new neuronal configuration at a pace that minimizes the pain and discomfort frequently associated with loss of a body part (i.e., phantom limb syndrome).

The present invention mitigates debilitating pain or discomfort by using AR sensory input to change the time necessary for neuronal remapping after loss of a limb. The invention provides flexibility as to the order, the areas, and the speed with which remapping may be accomplished, thus allowing the remapping to be modified in a manner that minimizes patient discomfort. For example, a below-the-knee amputee may utilize AR that simulates an intact leg. The AR displays an intact leg in real time. When the amputee thinks about moving the amputated limb, electrodes connected to the stump receive neural input, and the system simulates real time movement by the AR limb. The amputee has the illusion that they still have their amputated limb with full control over it.

In some aspects, force feedback and audio feedback may be used to increase the realism of user interaction with the simulated limb, for example, by allowing the user's hand to feel resistance and allowing the user to hear noise when the user scratches the simulated limb. Tactile stimulation of the virtual limb may be accomplished by neural input from electrodes, or force feedback on the portion of the limb above the amputation site. Over time, the visual and other aspects of the simulated limb may be faded out or altered so that the user's brain may remap the neuronal configuration, at a pace that does not induce pain or discomfort. These inventions, alone or in combination, serve to alleviate phantom limb pain and discomfort.

Furthermore, the instant invention may make it possible for prosthetic candidates to be virtually screened and fitted for the appropriate prosthetic solution. Additionally, the candidate may be trained with the instant system prior to receiving the permanent prosthetic. For instance, once the appropriate prosthetic solution or a number of optional solutions is determined by the system, said potential prosthetic solutions may be saved in the system's memory. The prosthetic candidate may then continue to compare and practice with the virtual model prosthetics. Once the most appropriate prosthetic is identified, the candidate may then continue to practice with the appropriate prosthetic so that once the real prosthetic is manufactured, the amputee may begin using the prosthetic limb in the real world with little to no learning curve.

These and other advantages of the present invention will become readily apparent from the detailed description below.

BRIEF DESCRIPTION OF THE DRAWINGS

Various non-limiting embodiments are further described with reference to the accompanying drawings in which.

DETAILED DESCRIPTION

Reference will now be made in detail to various embodiments of the invention, examples of which are illustrated in the accompanying drawings. While the invention will be described in conjunction with the following embodiments, it will be understood that the descriptions are not intended to limit the invention to these embodiments. On the contrary, the invention is intended to cover alternatives, modifications, and equivalents that may be included within the spirit and scope of the invention as defined by the appended claims. Furthermore, in the following detailed description, numerous specific details are set forth in order to provide a thorough understanding of the present invention. However, it will be readily apparent to one skilled in the art that the present invention may be practiced without these specific details. In other instances, well-known methods, procedures and components have not been described in detail so as not to unnecessarily obscure aspects of the present invention. These conventions are intended to make this document more easily understood by those practicing or improving on the inventions, and it should be appreciated that the level of detail provided should not be interpreted as an indication as to whether such instances, methods, procedures or components are known in the art, novel, or obvious.

For the sake of convenience and simplicity, the terms three-dimensional image, 3D image, 3D model, virtual limb and 3D virtual image may be used interchangeably herein, but are generally given their art-recognized meanings. Also, for convenience and simplicity, the terms pain, discomfort, and itching may be used interchangeably, and wherever one such term is used, it also encompasses the other terms.

As discussed in the background, people who have lost a body part may experience pain or other physical sensations as a result of phantom limb syndrome. An estimated 80% of amputees may experience phantom pain at some point during their lives. This condition is a result of an amputee perceiving pain in missing body parts. Sometimes the cause of pain may come from the muscle adjacent to the amputation point becoming clenched in an uncomfortable position. Many amputees may experience phantom limb sensations such as feeling as though the missing limb is being touched. The term phantom pain, in general, is a reference to the perception of pain in missing body parts, although it should be appreciated that the instant inventions are not limited to sensations of pain, but also may encompass other phantom sensations. Some amputees also experience a phenomenon referred to as telescoping, where the amputee perceives that their missing limb is growing shorter gradually over time. While phantom pain is most closely associated with amputated limbs, this very painful condition is experienced by many with body parts in general that no longer exist. Indeed, there are reports that the removal of the appendix, an organ not normally a source of any sensation or mental focus, may result in phantom pain. While this document utilizes the term "phantom limb pain", it should be understood to include similar or related phenomena.

The present invention relates to systems, devices and methods to provide immediate or near immediate relief from the pain and discomfort of phantom limb syndrome by generating a three-dimensional virtual image of the missing limb, and providing the amputee with the means to control the virtual limb in real or near real time.

Exemplary Methods of Treating Phantom Limb Syndrome

In one aspect, augmented reality technology is utilized to permit a person to see a missing limb. Such measures may be useful in reducing the symptoms of (or resolving) phantom limb syndrome. That is, when looking through the augmented reality technology (or otherwise using the augmented reality technology), the user is presented with some form of additional data that helps to mitigate the effects (or cause) of phantom limb syndrome.

In one implementation, a method of treating phantom limb syndrome comprises: (a) capturing data from a recording device operably coupled to a computing device and/or a display, the recording device configured to capture data associated with intact portions of a missing limb, one or more intact limbs and/or portions of an environment surrounding the missing limb; (b) identifying the data captured; (c) generating a three-dimensional virtual image of the missing limb and the surrounding environment from the data captured; and (d) displaying the three-dimensional virtual image and the portions of the surrounding environment to the amputee such that the missing limb appears intact.

Figure 1:
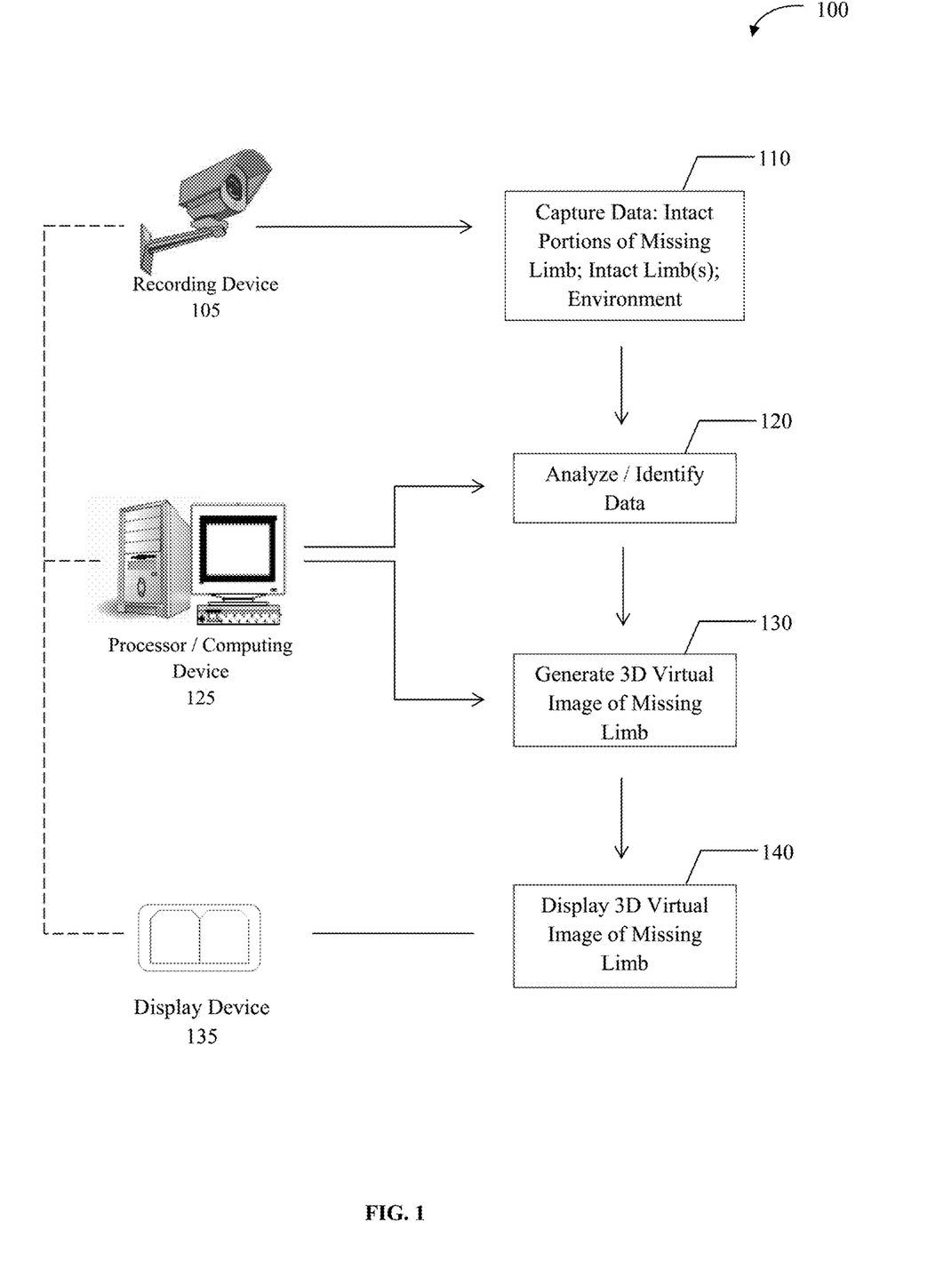
FIG. 1 schematically illustrates a method of treating phantom limb syndrome according to an embodiment of the present invention.

An exemplary system/method 100 is schematically illustrated in FIG. 1. The system may include a recording device 105, a processor/computing device 125, and a display device 135. In the embodiment of FIG. 1, the recording device 105 captures data associated with portions of the missing limb, one or more intact limbs and/or portions of the environment surrounding the missing limb. The processor/computing device 125 analyzes the data, identifies the data and/or images captured, and calculates and/or generates a three-dimensional virtual image of the missing limb and the portions of the surrounding environment from the captured data. The display device 135 generates and/or displays the three-dimensional virtual image of the missing limb and portions of the surrounding environment.

The recording device 105 in the exemplary embodiment of FIG. 1 may comprise one or more cameras, video recorders, audio recorders, spectrography equipment, medical measurement devices, and/or other devices that may be useful to capture data and/or images of the intact or missing limbs and/or environmental data. Processor/computing device 125 may be a conventional desktop or laptop computer, or many comprise any other type of device used for processing/computing functions (e.g., a notepad, tablet, smartphone, etc.) The display device 135 in the embodiments of the instant invention may comprise any type of display, including without limitation, a flexible display, wearable glasses, an LED display, an auto-stereoscopic display, a holographic display, a projector and screen, or other similar display. The display may, in some cases, be mounted, including, without limitation, on an adjustable table, platform or other structure, in a manner that allows the display to adjust to the needs of the amputee or the activity the amputee may be engaged in. The display may be connected to cameras, a microprocessor, antennae, electrodes, or other transmission, reception or similar devices.

The recording device 105 (e.g., one or more cameras) may be positioned at several angles above, below, or otherwise in line of sight with part of the adjustable platform and display in a manner that allows the cameras to capture every angle (or a desired number of angles) of the environment, the intact portions of the missing limb, any intact corresponding limb (e.g., a missing right arm and an intact left arm), or some subset of those elements. The cameras may be attached to the adjustable table, platform or other structure such that they are able to both rotate and slide if the system determines that more data is required to complete the modeling and rendering of the environment and the amputee's missing limb.

In one aspect, a light barrier may be utilized to block the amputee's missing limb from sight. The light barrier may be a stereoscopic monitor that does not require glasses for use. In one aspect, the light barrier may be anywhere on the spectrum from fully transparent to fully opaque. The camera system may record a 3D image and alter it for display on the monitor so that it appears to the amputee that their missing limb has been restored.

In some aspects, some or all of the AR presented to the patient may be generated artificially and/or from a group of one or more sets of images or videos. The images used to construct the AR, such as the environment and the limb, may be pulled from several sources, including but not limited to, databases such as the amputee's medical records, social media, photographs or other available media sources associated with the amputee or not associated with the amputee. The system may then pull this data, analyze it and render a model of the amputee's missing limb and the environment requested by the administrator. In one aspect, the image or images used may be modified programmatically or by a human, or a combination thereof. In another aspect, the imaging or image sources may be captured using a device capable of three dimensional capture. In another aspect, motion capture of the intact limb may be obtained and utilized to make the artificially generated image of the missing limb react in a manner that the user perceives as more natural or genuine.

In some implementations, the system may be set so that, by default, it captures the existing intact limb with its cameras in order to generate a 3D model of the reflection of the intact limb. In one aspect, even if the system is able to render a complete model of the amputee's missing limb using an existing limb, the system may compare the data used to generate the model to data from a database such as the amputee's medical records so as to detect any personally identifying mark that may exist on the missing limb, such as a birthmark, a tattoo, a scar or some other mark unique to the amputee. The system may then incorporate any personally identifying marks into the existing generated model to make the model appear to the amputee as close to the amputee's limb prior to amputation as possible. Where there is a mark on the intact limb but the mark did not also appear on the missing limb, the mark may be altered or removed by the system.

In some embodiments, the 3D virtual image may incorporate body alterations that do not currently appear on an intact limb, or that did not appear on the missing limb before it was amputated. For example, the user may desire a tattoo, piercing or other personally identifying mark on the 3D virtual image of the missing limb, and such image may be generated on the missing limb from images stored in one or more databases, or pulled from social media, the Internet and/or other sources. The body alteration may be a permanently or temporarily added alteration to the 3D image of the missing limb.

Figure 2:
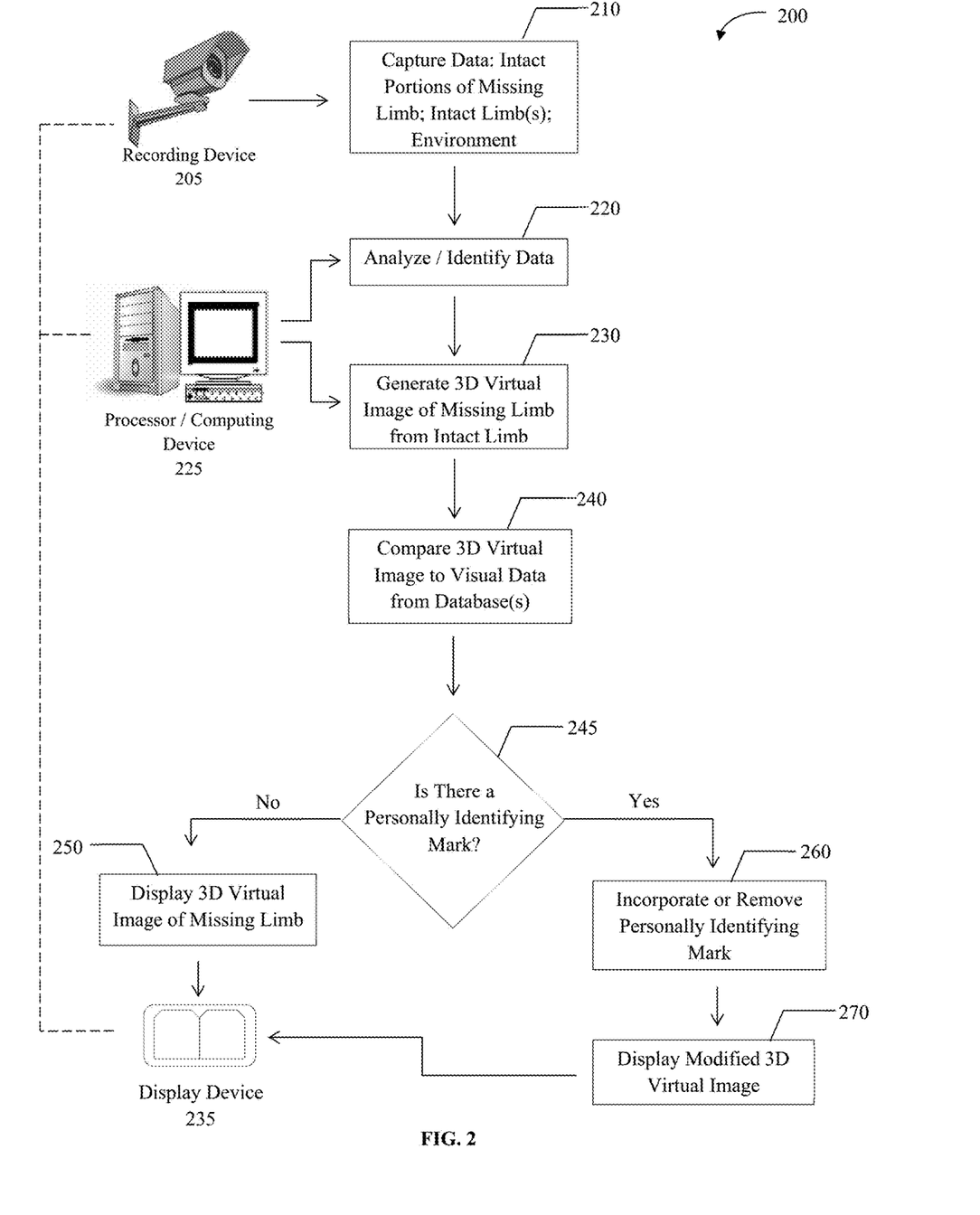
FIG. 2 schematically illustrates a method of incorporating personally identifying information into the virtual 3D image of the missing limb according to an embodiment of the present invention.

This embodiment is described in method 200 of FIG. 2. In the embodiment of FIG. 2, the system components comprise recording device 205, which is operably coupled to processor/computing device 225, which is further operably coupled to display device 235. Similar to the recording device 105 of FIG. 1, the recording device 205 may be one or more cameras, video recorders, audio recorders, spectrography instruments and/or equipment, medical measurement devices, and/or other devices that may be useful to capture data and/or images of the intact or missing limbs and/or environmental data. Processor/computing device 225 may be a conventional desktop or laptop computer, or many comprise any other type of device used for processing/computing functions (e.g., a notepad, tablet, smartphone, etc.) The display device 235 in the embodiments of the instant invention may utilize any type of display, including without limitation a flexible display, wearable glasses, an LED display, an auto-stereoscopic display, a holographic display, a projector, or other display.

The method begins at step 210. At step 210, data associated with intact portions of the missing limb, intact limb(s) and portions of the surrounding environment is captured by the recording device 205. At step 220, this data is analyzed and identified (e.g., by visual image recognition software) by the processor/computing device 225. Based on the data captured and analyzed, at step 230, the processor/computing device calculates and/or generates a 3D virtual image of the missing limb. At step 240, the 3D virtual image is compared with data extracted from one or more databases. The database(s) may be located on servers, including but not limited to medical record servers, penal system servers, workplace servers, servers associated with social media sites, cloud based servers, etc.

At step 240 it is determined whether there is a personally identifying mark on either the intact limb or on the missing limb. If there is not, then at step 250, the 3D image of the missing limb is displayed by display device 235. If there is a personally identifying mark on either the intact limb or the missing limb, then at step 260 the personally identifying mark is either incorporated in or removed from the 3D virtual image, depending on whether the mark had been on the missing limb before it was amputated, or whether it is on the intact limb, but was not on the missing limb.

In the event that the amputee lost both arms, both legs, or all limbs, the system may rely on data collected from media showing the amputee, before the incident that removed the amputee's limbs. If such data does not exist or may not be attainable, the system may render limbs based on the averaged, modal, or other data from other amputees. The system may make data selections for the averaging based upon the amputee's gender, height, weight, cultural background, musculature or other visual attributes such as skin color, which may be determined by the system's recording device (e.g. cameras). Based on the amputee's size the system may be able to determine the appropriate dimensions for the model based upon remaining structures such as the thigh, bicep, forearm or other body part of the amputee. In one aspect, it may be desirable to utilize family members in such a case.

Figure 3:
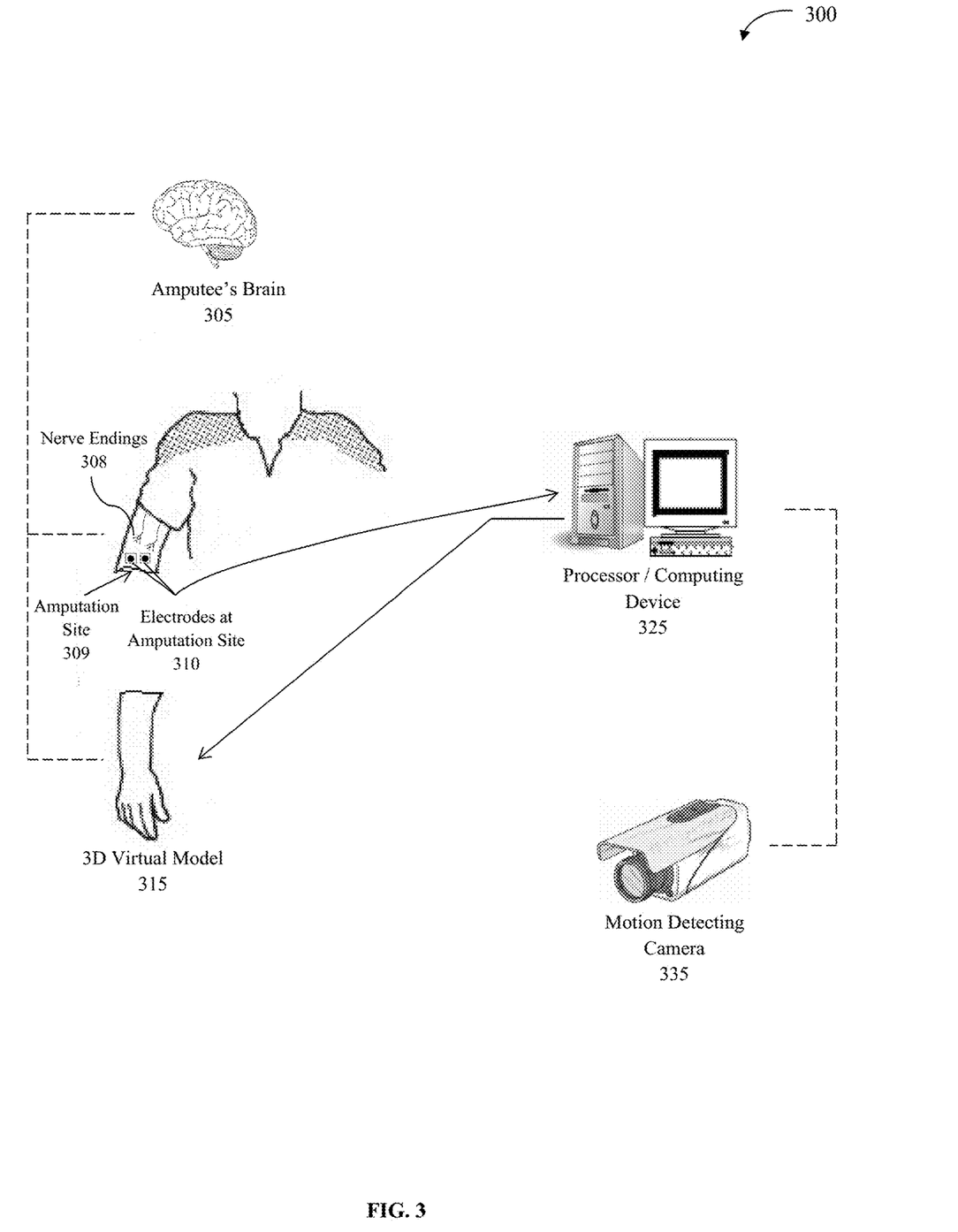
FIG. 3 schematically illustrates a method whereby the amputee may control the virtual 3D model as if the virtual 3D model were their own limb according to an embodiment of the present invention.

Referring now to FIG. 3, therein is shown another embodiment of a system 300 of the present invention. Electrodes 310 may be attached above the amputation site 309, or at another appropriate site (e.g., one identified by a clinician). The electrodes 310 may intercept electrical signals from the nerve endings 308 in the remaining muscular tissue at the amputation site 309. These electrical signals may be interpreted by the processor/computing device 325 and the appropriate movement may be made by the 3D virtual model 315. Effectively the amputee may control the virtual model 315 with their brain 305 as if the model 315 were their own limb. It should be understood that the reference to "attaching electrodes" is not meant to be limiting, and in fact additional mechanisms for reading or measuring neural signals are intended to be included in the use of that term, including mechanisms that do not require physical attachment.

Additionally, using a motion sensing 3D camera 335 (or other sensory devices), the system 300 may detect and recognize certain gestures, such as but not limited to, scratching, pinching, or poking the virtual limb. The recognition and registering of such a gesture may translate into tactile sensory stimulation of the virtual 3D model 315 that may be transmitted to the brain 305 of the amputee, such as by way of the electrodes 310 attached to the amputee's body at the amputation site 309, which measure and transmit nerve impulses. Consequently, when the system 300 recognizes tactile sensory stimulation of the virtual 3D model 315, the amputee may feel the stimulation as if the amputee's own body was being stimulated. The system 300 may be able to recognize such tactile stimulation by both remaining aware of where the virtual 3D model 315 is in space in relation to the surrounding environment and by mapping out and integrating virtual biologically accurate and/or responsive nerve systems into the virtual limb model 315. Additionally, in some aspects force feedback may be applied on the portion of the limb that has not been amputated to allow the user to feel scratching, pinching and/or poking of the amputated limb.

In some instances, visual stimulation may be recognized by the amputee and translated into tactile sensory stimulation of the missing limb. For example, a virtual heating pad on the missing limb (and/or an actual heating pad element on the intact portion of the missing limb) may stimulate the amputee's brain to feel warmth in the area of the missing limb. Similarly, a cold sensation on an intact limb and/or the intact portion of the missing limb (e.g., ice applied to the intact limb) and virtual ice applied to the 3D image of the virtual limb, may stimulate the amputee to feel cold in the missing limb. The ability of the virtual limb model 315 to register sensory stimuli, visual or otherwise may make it possible for the virtual limb 315 to respond to virtual environment changes, including, but not limited to temperature changes, pressure and texture.

For instance, the virtual environment around a virtual leg may be changed by input into the system to make the environment around the leg appear cold to the amputee's eyes and feel cold to the touch of the virtual leg. In another aspect the virtual environment may change such that the virtual limb appears to be resting in a bucket of warm water. In this scenario, the amputee may feel the virtual warmth of the virtual water and its wetness. Furthermore, the amputee may feel the virtual coarseness of the edge of the galvanized bucket as the amputee removes the virtual leg from the bucket and rests it on the real floor. Using cameras and thermal imaging the system may recognize when the virtual foot has made contact with the real floor and allow the amputee to feel the floor's coolness and gradually drop the temperature of the warm virtual foot in response. Further, when "touching" the virtual limb with an intact limb (e.g., an intact hand), such touching may create a tactile sensation in the missing limb. For example, the amputee may apply a real (or virtual) ice pack to the missing limb. The actual cold sensation from a real ice pack against the amputee intact hand (or the image of the virtual ice pack touching the virtual limb) may create the feeling of cold in the virtual limb. In some aspects this level of sensitivity may make the virtual limb indistinguishable from a real limb.

In some embodiments, a sample of the amputee's DNA may be taken, the DNA sequences read, analyzed and/or compared with other DNA markers, and the appearance, musculature, texture, etc. of the amputated limb may be recreated based on the characteristics of the amputee's DNA. In the future, it may be possible to create a "real" limb, based on a sample of an intact limb of the amputee, or other part of the amputee's body.

In some embodiments, a person suffering from phantom limb syndrome may wear augmented reality glasses, augmented reality contact lenses, or other means of augmenting perception, and a realistic image of a limb may be presented through the augmented reality glasses, contact lens, or other means. As the phantom limb pain becomes mitigated as a result of seeing the artificially generated image of a limb, the image may be altered, for example by making it semi-transparent. The image of the limb may be altered over time so that it appears, over some period of time, to fade out.

For example, over the course of six months a user may spend the first week with a fully opaque image of a limb, and then the image would fade by some amounts daily until it simply disappears at the end of the time period. When this technology is used in clinical setting, a physician's order, patient self-reported pain, or directly measured data (e.g., measuring nerve impulses) may be used to determine the rate at which the limb would fade, shrink or otherwise become diminished over time. In addition to or in place of changing opacity, the limb size or other characteristics may be changed over time, for example by shrinking the limb by 1 mm per day or by virtually "amputating" 1 mm of the limb each day until the virtual amputation point reaches the actual amputation point.

Figure 4:
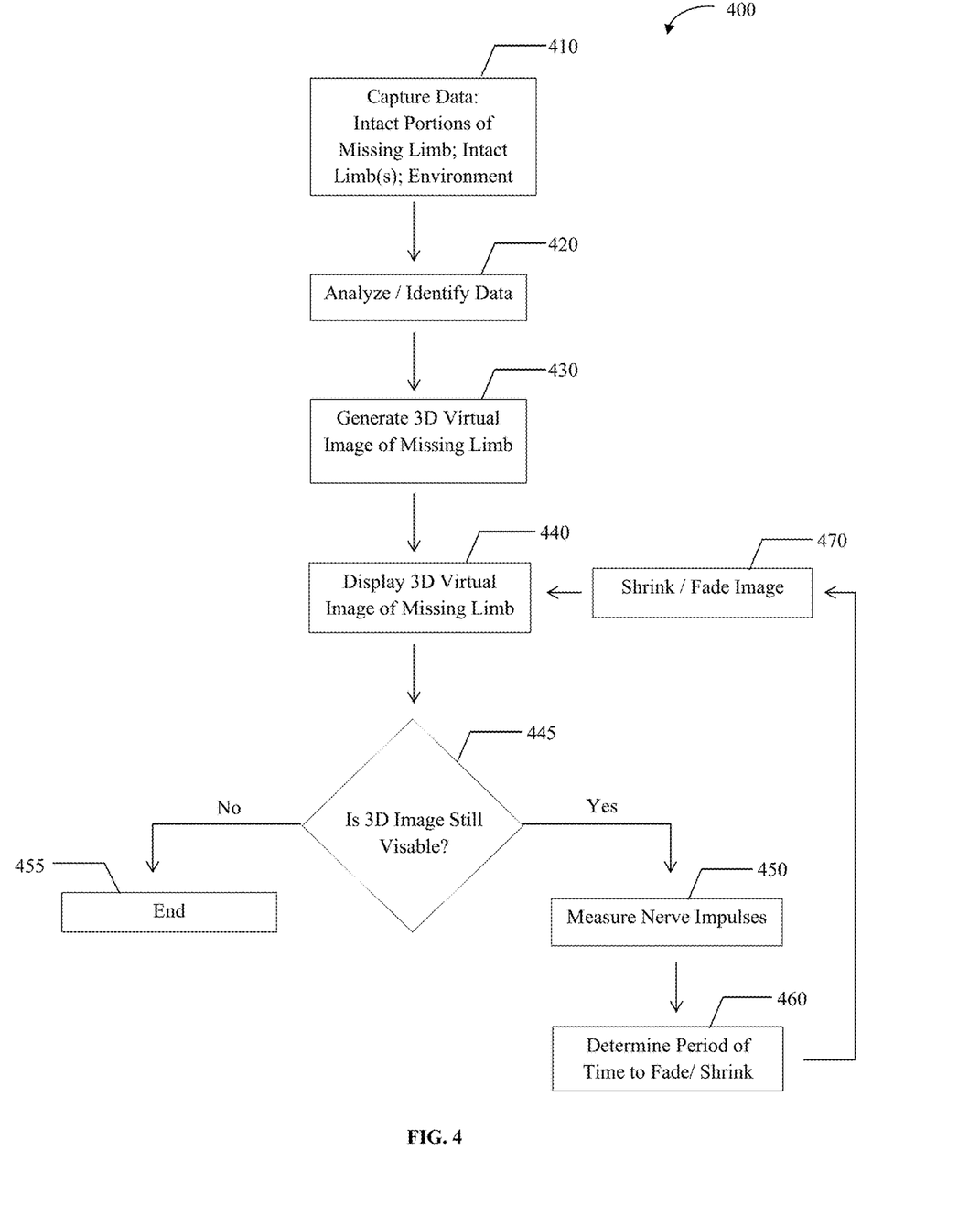
FIG. 4 schematically illustrates a method whereby the virtual 3D image of the missing limb shrinks or fades over time based on the measurement of nerve impulses according to an embodiment of the present invention.

The method 400 of FIG. 4 schematically illustrates altering an image of a virtual limb over time. The method begins at step 410 where data associated with intact portions of the missing limb, intact limbs and portions of the surrounding environment are captured. The data may be captured by one or more cameras, video recorders, audio recorders, spectrography equipment, medical measurement devices, and/or other devices that may be useful to capture data and/or images of the intact or missing limbs and/or environmental data. At step 420, the data is analyzed and identified (e.g., by visual image recognition software). At step 430, the captured data is utilized to calculate and/or generate a 3D virtual image of the missing limb. Then, at step 440, the 3D image of the missing limb is displayed to the amputee (e.g., by use of flexible display, wearable glasses, an LED display, an auto-stereoscopic display, a holographic display, a projector and screen, etc.).

At step 445, a determination is made as to whether the 3D image is still visible. If not, and the amputee's phantom limb syndrome has been alleviated, then the method ends at step 445. On the other hand, if the image is still visible, at step 450, nerve impulses are measured (e.g., by use of electrodes attached at the amputation site and operably coupled to a processing device configured to interpret the signals) to determine the level of the amputee's discomfort and/or pain, and at step 460, the time period and/or rate at which to shrink or fade the 3D virtual image is determined. At step 470, the 3D virtual image is altered (e.g., by shrinking, fading and/or changing the opacity of the image) and the image is again displayed to the amputee. The method continues to repeat the steps 440 through 470 until the 3D virtual image is no longer visible and/or the amputee no longer experiences pain or discomfort in the missing limb.

It should be noted that with regard to the embodiments described herein, that in the future, direct neural input may make it possible to transmit images or other sensory data directly to a person's brain, and such technology could be used as a transmission modality for some aspects of these inventions.

Exemplary Methods for Screening Prosthetic Limbs

This type of sensitivity and flexibility within the instant invention may lend the system to prosthetic limb screening processes. Prosthetic limb candidates may interface with the system to determine in advance what kind of prosthetic would be best for the candidate. Furthermore, the system may return appropriate dimensions for an aesthetically realistic prosthetic model that may allow for the production of aesthetically appropriate custom limbs, that do not require extensive fitting and refitting after the limbs are manufactured. Additionally the instant invention may be able to be used to train amputees in using a prosthetic before it is even manufactured and fitted. The system may also be used to train others, such as the amputee's family or other members of the general public or to give them a sense of what the amputee will experience.

In addition, the present invention may be utilized to provide input to infants and very young children who are born missing a limb or who otherwise lose a limb or limb function. Such children may be too young, growing too fast, or otherwise unable to utilize an actual prosthetic limb. However, the period of neuronal plasticity during which a human's brain is initially mapped in a manner permitting effective control of the body often coincides with the period during which the child is not a good candidate for fitting with a prosthetic limb. Thus, the system may be used to fit an appropriate virtual prosthetic limb to the child.

By utilizing the inventions described herein, the child's brain may develop in a manner that will allow the child to far more effectively and naturally control a prosthetic limb by giving the child the ability to interact with a virtual prosthetic limb. In one aspect, where a child has poor control of a limb but is expected to eventually obtain better control, such as in cases where there is a broken limb, muscle damage, or other non-permanent injury, the child's development of the ability to control that limb may be allowed to continue utilizing the instant inventions, even during the period where the physical limb is unable to properly function.

Once a suitable prosthetic has been decided upon, to then be manufactured for the child's use in the real world, the child's parent may be virtually fitted for the same virtual model of the prosthetic using the system to scale the model up to the appropriate size for the parent. The system may then virtually train the parent on how to appropriately use the prosthetic so that they may empathize with their child, and be able to aid their child in getting used to the prosthetic if the child were too young to do this learning for themselves.

Exemplary Systems and Devices for Treating Phantom Limb Syndrome

Aspects of the present invention also relate to devices to mitigate the debilitating pain or discomfort of phantom limb syndrome by using augmented reality ("AR") to shorten the time necessary for neuronal remapping after loss of a limb. In an exemplary embodiment, the device comprises (a) one or more recording devices configured to capture intact portions of a missing limb, one or more intact limbs and/or portions of an environment surrounding the missing limb; (b) a processing and/or computing device operably coupled to the one or more recording devices, the processing and/or computing device configured to analyze and/or identify the data captured, and (c) a display operably coupled to the computing device configured to generate a three-dimensional virtual image of the missing limb, such that the missing limb appears intact to the amputee.

Figure 5:
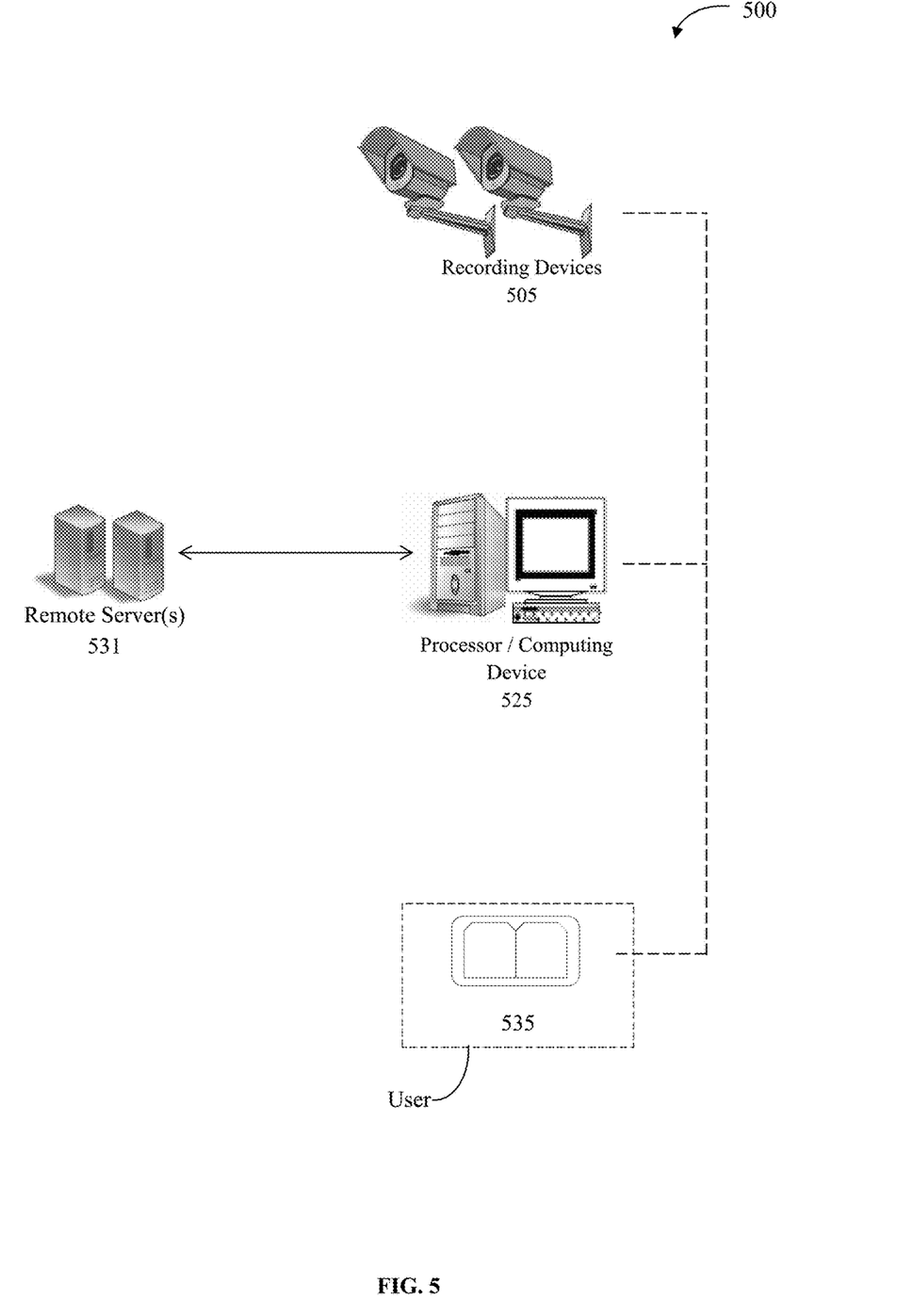
FIG. 5 schematically illustrates a system and devices for treating phantom limb syndrome according to an embodiment of the present invention.

Referring now to FIG. 5, therein is shown an embodiment of a system 500 for treating phantom limb syndrome. In the embodiment of FIG. 5, one or more recording/capturing devices 505 (e.g., one or more cameras, video recorders, audio recorders, spectrography devices, medical measurement devices, and/or other devices that may be useful to capture data and/or images of an intact limb, portions of a missing limb and/or environmental data) are operably coupled to a processor/computing device 525. Operably coupling may comprise, directly coupling the recording/capturing devices, or may comprise coupling via near field communication, Bluetooth, a local area network, a Wi-Fi network, a cellular network, a wide area network, etc. The processor/computing device 525, may be any device with which data may be analyzed, identified and/or stored (e.g., a desktop computer, a tablet, a notepad, a laptop, a personal digital assistant (PDA), a smartphone, etc.).

In the embodiment shown in FIG. 5, the processor/computing device may also access remote servers 531 and/or other devices to access data about the amputee, his or her missing limb(s) and/or other information useful to analyzing, identifying and/or generating a 3D virtual image of the missing limb. For example, the processor/computing device may access medical record servers, penal system servers, workplace servers, servers associated with social media sites, cloud based servers, etc.

Display device 535 is operably coupled to processor/computing device 525 by any of the means described above. The display device may comprise a flexible display, wearable augmented reality glasses, an LED display, an auto-stereoscopic display, a holographic display, a projector and screen, or any other device capable of generating and/or displaying a three-dimensional virtual image of a missing limb and portions of the surrounding environment. The display may, in some instances, be mounted, including, without limitation, on an adjustable table, platform or other structure (not shown), in a manner that allows the display to adjust to the needs and/or line of sight of the amputee. The display may also be connected to other transmission/reception devices (e.g., one or more DVD's VCR's, audio players, etc.).

Additionally, the recording devices 505 may be positioned at several angles above, below, or otherwise in line of sight with part of the adjustable table, platform or other structure and the display in a manner that allows the cameras to capture every angle (or a desired number of angles) of the environment, the intact portions of the missing limb, any intact corresponding limb (i.e. a missing right arm and an intact left arm), or some subset of those elements. The recording devices 505 may be attached to the structure such that they are able to both rotate and slide if the system determines that more data is required to complete the modeling and rendering of the environment and the amputee's missing limb.

In one aspect, a light barrier (not shown in FIG. 5) may be utilized to block the amputee's missing limb from sight. The light barrier may be a stereoscopic monitor that does not require glasses for use. The recording device(s) 505 may record a 3D image and alter it for display on a monitor so that it appears to the amputee that their missing limb has been restored. In some aspects, some or all of the augmented reality presented to the amputee may be generated artificially and/or from a group of one or more sets of images or videos.

The foregoing descriptions of specific embodiments of the present invention have been presented for purposes of illustration and description. They are not intended to be exhaustive or to limit the invention to the precise forms disclosed. Obviously, many modifications and variations are possible in light of the above teaching. The embodiments were chosen and described in order to best explain the principals of the invention and its practical application, to thereby enable others skilled in the art to best utilize the invention and the various embodiments and modifications as are suited to the particular use contemplated. It is intended that the scope of the invention be defined by the components and elements described herein and their equivalents.

What is claimed is:

1. A method of treating phantom limb syndrome in an amputee, the method comprising:
capturing data from a recording device operably coupled to a computing device and/or a display, the recording device configured to capture data associated with intact portions of a missing limb, one or more intact limbs and/or portions of an environment surrounding the missing limb;
analyzing and/or identifying the data captured;
generating a three-dimensional virtual image of the missing limb from the data captured;
displaying the three-dimensional virtual image to the amputee such that the missing limb appears intact;
decreasing an opacity of the three-dimensional virtual image over a period of time so that it appears to fade out; and
measuring nerve impulses and determining from the nerve impulses the period of time over which the three-dimensional virtual image of the missing limb fades out.

2. The method of claim 1, wherein the display is a flexible display, wearable augmented reality glasses, augmented reality contacts, an LED display, an auto-stereoscopic display, a hologram, or a projector and screen.

3. The method of claim 1, wherein the data captured from the recording device includes at least one of the intact portions of the missing limb.

4. The method of claim 1, wherein the data captured from the recording device includes at least one of the one or more intact limbs.

5. The method of claim 1, further comprising altering the three-dimensional virtual image of the missing limb over a period of time so that it appears to shrink.

6. The method of claim 1, further comprising comparing the three-dimensional virtual image of the missing limb to visual data from one or more databases to identify a personally identifying mark on the missing limb or intact limb(s).

7. The method of claim 6, further comprising incorporating the personally identifying mark on the missing limb into the three-dimensional virtual image of the missing limb.

8. The method of claim 6, further comprising removing the personally identifying mark on the intact limb from the three-dimensional virtual image of the missing limb.

9. The method of claim 1, wherein the three-dimensional virtual image is generated from data collected from media showing the amputee before the amputee had one or more limbs amputated.

10. The method of claim 1, wherein the one or more intact limbs comprise at least two limbs from other people, and generating the three-dimensional virtual image of the missing limb comprises averaging the at least two limbs from the other people.

11. The method of claim 1, further comprising:
attaching electrodes above an amputation site or another site on the amputee's body, wherein the electrodes are configured to intercept electrical signals from nerve endings above the amputation site; and
moving the three-dimensional virtual image of the missing limb in real or near-real time based on an interpretation of the electrical signals.

12. The method of claim 1, further comprising:
operably connecting one or more motion sensing devices to the display, the motion sensing device(s) configured to detect and recognize one or more gestures; and
stimulating the three-dimensional virtual image of the missing limb such that the stimulation is transmitted to the amputee's brain and the amputee feels the stimulation.

13. The method of claim 1, further comprising mapping and integrating virtual biologically-accurate and/or responsive nerve system data into the three-dimensional virtual image.

14. The method of claim 1, wherein the data captured from the recording device includes at least one of the portions of the environment surrounding the missing limb.

15. The method of claim 1, wherein generating the three-dimensional image of the virtual environment includes generating the environment and displaying the three-dimensional virtual image includes displaying the environment.

16. The method of claim 1, where the data captured is identified.

17. A method of treating phantom limb syndrome in an amputee, the method comprising:
capturing data from a recording device operably coupled to a computing device and/or a display, the recording device configured to capture data associated with intact portions of a missing limb, one or more intact limbs and/or portions of an environment surrounding the missing limb;

analyzing and/or identifying the data captured;

generating a three-dimensional virtual image of the missing limb from the data captured;

displaying the three-dimensional virtual image to the amputee such that the missing limb appears intact; and comparing the three-dimensional virtual image of the missing limb to visual data from one or more databases to identify a personally identifying mark on the missing limb or intact limb(s).

18. A method of treating phantom limb syndrome in an amputee, the method comprising:

capturing data from a recording device operably coupled to a computing device and/or a display, the recording device configured to capture data associated with intact portions of a missing limb, one or more intact limbs and/or portions of an environment surrounding the missing limb;

analyzing and/or identifying the data captured;

generating a three-dimensional virtual image of the missing limb from the data captured;

displaying the three-dimensional virtual image to the amputee such that the missing limb appears intact, wherein the three dimensional image is generated from data collected from media showing the amputee before the amputee had one or more limbs amputated.

* * * * *